United States Patent [19]

Agrawal et al.

[11] Patent Number: 4,462,992
[45] Date of Patent: Jul. 31, 1984

[54] NITROIMIDAZOLE RADIOSENSITIZERS FOR HYPOXIC TUMOR CELLS AND COMPOSITIONS THEREOF

[75] Inventors: Krishna C. Agrawal; Masakazu Sakaguchi, both of New Orleans, La.

[73] Assignee: Research Corporation, New York, N.Y.

[21] Appl. No.: 346,914

[22] Filed: Feb. 8, 1982

[51] Int. Cl.[1] .................. A61K 31/70; C07H 19/08
[52] U.S. Cl. ................................ 424/180; 536/23; 548/338
[58] Field of Search ..................... 536/23; 424/180

[56] References Cited

U.S. PATENT DOCUMENTS 3,646,057  2/1972  Beaman et al. ................ 424/267
4,282,232  8/1981  Agrawal ........................ 424/267

OTHER PUBLICATIONS

Guglielmi et al., *Chemical Abstracts*, vol. 89, 1978, p. 560, Abstract No.:6487y.

*Primary Examiner*—Johnnie R. Brown
*Assistant Examiner*—Elli Peseler
*Attorney, Agent, or Firm*—Scully, Scott, Murphy & Presser

[57] ABSTRACT

Compounds of the formula:

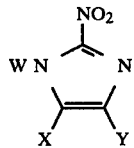

wherein W is selected from the group consisting of

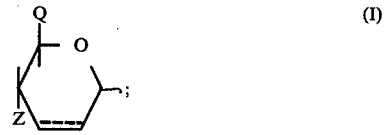 (I)

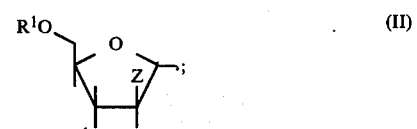

(II)

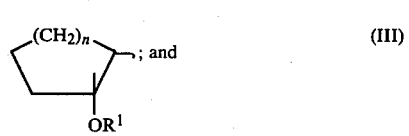

(III)

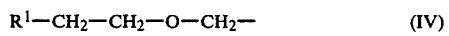

(IV)

Wherein
Q is hydrogen or $-CH_2OR^1$;
Z is hydrogen or $-OR^1$;
n is 1 or 2;
wherein $R^1$ are the same or different radicals selected from the group consisting of hydrogen, and

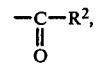

where $R^2$ is lower alkyl, aryl, or aralkyl; wherein the bond at positions 2' and 3' of structure I may be single or double; or it may be a C-nucleoside attached at 3' position of the sugar; X and Y are the same or different selected from the group consisting of hydrogen, an electron withdrawing group, and a group wherein X and Y taken together form a 6-membered carbocylic aromatic ring, are useful as radiosensitizing agents during x-ray radiotherapy of tumor cells.

37 Claims, No Drawings

NITROIMIDAZOLE RADIOSENSITIZERS FOR HYPOXIC TUMOR CELLS AND COMPOSITIONS THEREOF

BACKGROUND OF THE INVENTION

Funds from National Institutes of Health grant No. CA-21050 were used in the development of this invention.

1. Field of the Invention

The present invention relates to novel nitroimidazole radiosensitizers useful for radiation therapy of tumor cells.

2. Description of the Prior Art

One of the most serious problems encountered during the X-ray radiotherapy of tumors is the relative resistance of hypoxic tumor cells to destruction. This radio-resistance is directly related to the lack of oxygen in these cells, and X-ray doses have to be about three times higher to kill a given proportion of hypoxic cells than of well oxygenated cells. Oxygen is the main radiosensitizer during X-ray therapy. The presence of hypoxic cells has been demonstrated repeatedly in animal tumors and results in resistance to radiation, which makes cures with a single dose of X-rays difficult or impossible. (Adams, G. E. et al, Chemotherapy, Vol. 7:187-206 (1976)). The resistance is also a serious limitation in attempts to increase the therapeutic ratio between tumor and normal tissue damage in radiotherapy. This disadvantage of hypoxic cells is reduced in tumors which can reoxygenate their hypoxic cells during fractionated radiotherapy, for example by shrinkage. It is probably reoxygenation during the course of radiation therapy which enables cures to be achieved at the present time.

To overcome the problem of hypoxia one proposed solution is to carry out radiation treatment with patients in high pressure oxygen (HPO) chambers. Although much experience has been gathered with this method, it is cumbersome and slow in its use. The shut-down of blood vessels is also a serious problem associated with this method.

A solution to the problem of radiosensitization of hypoxic tumor cells, has been the use of fast neutron or $\pi$ meson radiation, rather than X-rays. Although neutrons are quite effective in tumors, the method is very expensive since it requires extensive facilities not readily available to most hospitals. Furthermore, the OER (oxygen enhancement ratio) for neutrons or pions is only 1.5-1.7. The OER is the ratio of the slopes of the linear portions of the survival curves in the presence of radiosensitizer (or oxygen) compared to that in anoxia with no drug present. The higher the OER the better the radiosensitizer approaches the effect of oxygen.

The third solution is the use of compounds which simulate oxygen in their ability to radiosensitize tumor cells. These compounds are provided externally and diffuse throughout the body. Because of this general distribution, it is important that they cause more damage to tumor cells than to normal tissue cells. Sensitization by DNA intercalating drugs, such as 5-bromodeoxyuridine and 5-flourodeoxyuridine has been investigated, but the compounds failed precisely because of their poor selectivity problems.

In 1963, Adams et al, Biophysic. Res. Comm. 12:473 (1963) proposed that the ability of compounds to sensitize hypoxic bacterial cells is directly related to their electron affinity. This idea has been generally verified and has aided the search for more active compounds.

Nitrofurans, for example, are active in vitro for the radiosensitization of mammalian hypoxic cells. Since their metabolic half life is only a few minutes, however, they are not useful clinically (Chapman, J. D. et al, Cancer Research, 32:2616 (1972).

Further searches for other drugs already in clinical use and posessing a chemical structure with electron affinity, led to the discovery in 1973 of the radiosensitization action of metronidazole (1) by Foster and coworkers (Foster, J. L. and Wilson, R. L., Brit. J. Radiol., 46:234 (1973):

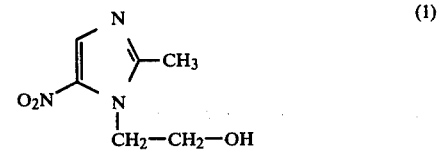

Metronidazole is active both in vivo and in vitro.

Another nitroimidazole sensitizer, misonidazole (2), has also recently been proven to be of value (Asquith, J. D., et al, Rad. Ras. 60:108 (1974)):

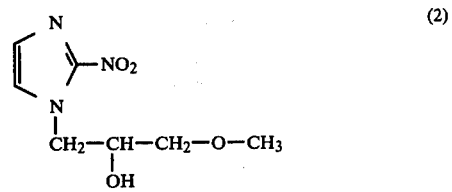

Both metronidazole and misonidazole are effective in vivo. However, both compounds show serious side effects when administered orally. They exhibit peripheral neuropathy and convulsions in mice, and their central nervous system toxicity is a limiting factor for their use in humans.

Recently, Agrawal, U.S. Pat. No. 4,282,232 disclosed nitroimidazole and nitrobenzimidazole compounds containing N-oxide functionalities. These compounds were useful as radiosensitizing agents and had decreased central nervous system toxicity. Agrawal and coworkers disclosed, at the 179th meeting of the American Chemical Society in Houston, Texas in March of 1980, nitroimidazole containing nucleosides such as 1$\beta$-D-glucopyranosyl, 1-$\beta$-D-gluco-thiopyranosyl and also a neuraminic acid derivative of 2-nitroimidazole.

A need continues to exist for a biologically active and clinically useful radiosensitizing compound for the radiation treatment of tumor cells, and which will show low central nervous system toxicity.

SUMMARY OF THE INVENTION

It is therefore an object of the invention to provide a radiosensitizing compound for the radiotherapy of tumor cells which is stable and biologically active.

Another object of the invention is to provide a radiosensitizing compound of hypoxic tumor cells which shows low central nervous system toxicity.

A further object of the invention is to provide a radiosensitizing compound of hypoxic tumor cells which has high electron affinity.

Still another object of the invention is to provide a process for preparing a radiosensitizing compound useful in the X-ray radiotherapy of tumor cells.

Yet another object of the invention is to provide a pharmaceutically active composition, useful in radiosensitization of hypoxic tumor cells.

These and other objects of the invention which will hereinafter become more readily apparent have been achieved by providing biologically active hypoxic cell radiosensitizing compounds of the formula:

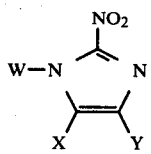

wherein W is selected from the group consisting of

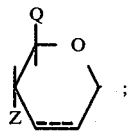 (I)

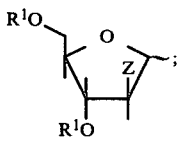 (II)

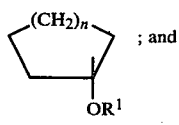 ; and (III)

 (IV)

wherein
Q is hydrogen or —CH$_2$OR$^1$;
Z is hydrogen or —OR$^1$;
n is 1 or 2;
wherein R$^1$ are the same or different radicals selected from the group consisting of hydrogen and —C(O)—R$^2$ where R$^2$ is lower alkyl, aryl, or arylalkyl; the bond between carbons 2' and 3' of structure I may be single or double;
X and Y are the same or different selected from the group consisting of hydrogen, an electron withdrawing group and a group wherein X and Y taken together form a six membered carbocyclic aromatic ring.

DESCRIPTION OF THE PREFERRED EMBODIMENTS

The compounds of the present invention are nucleoside derivatives and analogues of 2-nitroimidazole or 2-nitrobenzimidazole. The nucleoside derivatives can be either hexopyranosyl, arabinofuranosyl rings or fully carbocyclic analogues thereof, or acyclic analogues thereof. One of the characteristics of the compounds of the present invention is that at most they contain no more than 2-3 hydroxy groups. Applicants have discovered that when compounds have more than three hydroxy groups in the sugar portions of the molecules, (see e.g. Agrawal et al, 179th ACS Meeting, supra) the radiosensitization activity decreases.

The compounds of the present invention comprise those having the formulae:

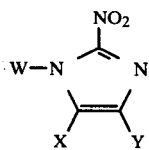

wherein W is selected from the group consisting of:

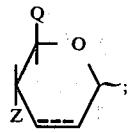 (I)

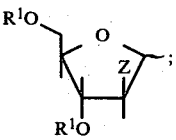 (II)

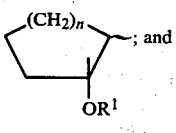 ; and (III)

 (IV)

wherein
Q is hydrogen or —CH$_2$OR$^1$;
Z is hydrogen or —OR$^1$;
n is 1 or 2:
wherein R$^1$ are the same or different radicals selected from the group consisting of hydrogen and —C(O)—R$^2$, wherein R$^2$ is lower alkyl, aryl, or arylalkyl; the bond between carbons 2' and 3' of structure I may be single or double;
X and Y are the same or different and selected from the group consisting of hydrogen, electron withdrawing substituents designed to enhance the final electron affinity of the compounds, and a group wherein X and Y taken together form a 6-membered carbocyclic aromatic ring.

Among the preferred lower alkyl radicals R$^2$ are the C$_1$-C$_4$ alkyl radicals. Among the preferred aryl radicals R$^2$ are phenyl, nitrophenyl, chlorophenyl, lower alkyl substituted phenyl, lower alkoxy substituted phenyl, and the like. Among the preferred aralkyl radicals R$^2$ are benzyl, nitrobenzyl, halobenzyl and the like.

X and Y may be electron withdrawing substituents selected from the group consisting of nitro; R$^3$—CO— where R$^3$ is C$_1$-C$_4$ alkyl; nitrile; carboxyamide (NH$_2$—CO—)); carboxyalkyl of the type R$^4$O—CO— wherein R$^4$ is C$_1$-C$_4$ alkyl; nitrone of the type R$^5$—N(O)=CH— wherein R$^5$ is C$_1$-C$_4$ alkyl; hydroxymethyl (HO—CH$_2$—); nitrilomethyl (NC—CH$_2$—); 2-phenylvinyl and 2-(nitrophenyl)vinyl.

When the compounds are fully acylated at the hydroxy groups of the nucleoside (or analogue) portion of the molecule, their aqueous solubility is decreased, although they retain radiosensitization activity. Thus, among the most preferred compounds of the invention are those wherein the hydroxy groups at the nucleoside portions of the molecules are free i.e., those molecules wherein $R^1$ is hydrogen.

A preferred subclass of compounds is that wherein the nucleoside moiety is an arabinofuranosyl, and only the 5'—OH group is esterified; i.e. arabinofuranosyl compounds with 2 free hydroxy groups.

Other preferred embodiments of the invention are those compounds wherein the stereochemistry around C-1 of the nucleoside (or cyclic analogue) moiety is in the α configuration. A further preferred embodiment are those compounds wherein X=Y=hydrogen.

Another preferred subclass of compounds is that wherein a carbocyclic nucleoside analogue is present having 5 or 6 carbon atoms in the ring and a hydroxy group at position 2'.

Specific preferred compounds of the present invention are:

1-(2',3'-didehydro-2',3'-dideoxy-α-D-erythro-hexopyranosyl)-2-nitroimidazole;
1-(2',3'-didehydro-2',3'-dideoxy-β-D-erythro-hexopyranosyl)-2-nitroimidazole;
1-(α-D-arabinofuranosyl)-2-nitroimidazole;
1-(β-D-arabinofuranosyl)-2-nitroimidazole;
1-(2',3'-dideoxy- or -D-erythro-hexopyranosyl)-2-nitroimidazole;
α and β forms of 1-(4',6'-di-O-acetyl-2',3'-didehydro-2',3'-dideoxy-D-erythro-hexopyranosyl)-2-nitroimidazole;
α and β forms of 1-(2',3',5'-tri-O-benzoyl-D-arabinofuranosyl)-2-nitroimidazole.
1-(2-deoxy-α-D-erythro-pentofuranosyl)-2-nitroimidazole;
1-(2-deoxy-β-D-erythro-pentofuranosyl)-2-nitroimidazole;
1-(tetrahydro-2-furanyl)-2-nitroimidazole;
1-(tetrahydro-2-pyranyl)-2-nitroimidazole;
1-(2-hydroxycyclopentyl)-2-nitroimidazole;
1-(2-hydroxycyclohexyl)-2-nitroimidazole;
1-[(2-hydroxyethoxy)methyl]-2-nitroimidazole.

The hydroxylated pyranosyl or furanosyl compounds of the present invention can be prepared by standard nucleophilic reactions of the 2-nitroimidazole derivatives with corresponding pyranosyl or arabinofuranosyl derivatives according to the following scheme:

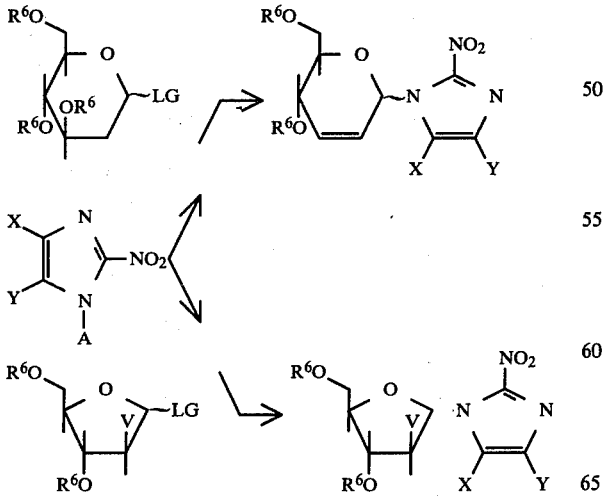

In this scheme, LG is any leaving group capable of undergoing bimolecular nucleophilic (SN2) substitution by the N-1 nitrogen atom of the imidazole ring. Preferably, LG is a halide, such as —F, Cl, —Br,; or a tosyl group or an acyl group.

The wiggled bond ("∼") indicates that it is possible to start with a stereochemical mixture at position C-1' of the nucleoside, and obtain a mixture of the 2-nitroimidazole nucleosides. It is of course also possible to start with substantially pure stereochemical compounds at position C-1', and only obtain the α or β nucleosides respectively. A represents hydrogen or a TMS (trimethylsilyl) group used to protect one of the two nitrogen atoms of the 2-nitroimidazole. Other nitrogen-protecting groups can of course be used, especially acid labile ones. In the scheme, V is hydrogen or $OR^6$ where $R^6$ is an acyl radical —C(O)—$R^7$ wherein $R^7$ is preferably a lower alkyl or aryl, preferably methyl or phenyl.

The preparation of the arabinofuranosyl derivatives is carried out in the presence of mercuric bromide, and the separation of the α or β compounds can be carried out by standard chromatographic techniques, such as preparative thin layer chromatography. An alternative method of preparation for the arabinofuranosyl derivatives is carried out by the condensation reaction of unprotected 2-nitroimidazole with 1-acetyl-2,3,5-tri-O-benzoyl arabinofuranose (Korbukh, I. A. et al, Zh. Org. Khim., 13, 73 (1977)) in the presence of stannic chloride and mercuric bromide (or mercuric cyanide).

The preparation of the hexopyranosyl derivatives is carried out in the presence of stannic chloride, and separations can be carried out as above.

The condensation of the 2-nitroimidazole reactant with the hexopyranosyl nucleoside containing the leaving group LG results in formation of the double bond at the 2' position, by simultaneous deacylation.

Deprotection of the acylated derivatives to yield free hydroxy containing molecules is carried out in base such as, for example, methanolic methoxide or methanolic ammonia.

An alternative method of preparation for the hexopyranosyl compounds is the direct condensation of unprotected 2-nitroimidazole with 3,4,6-tri-O-acetyl glucal, following the fusion methods reported by Bowles et al (Journal of the American Chemical Society, 86:1252 (1964)), and Leutzinger et al, (Tetrahedron Letters, 43:4475 (1968)):

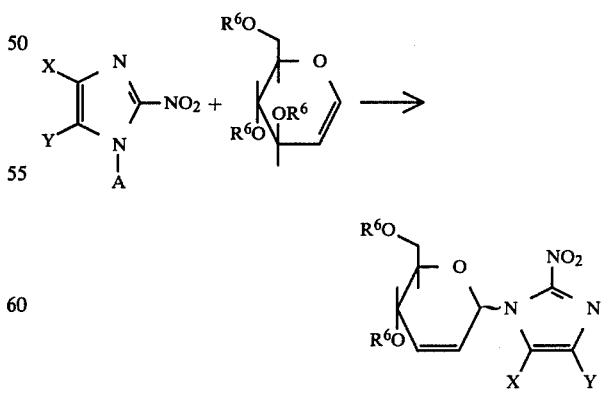

The leaving group-containing arabinofuranose or hexopyranose starting materials are readily available (for example, see Fletcher, H. G., Jr., Meth. Carbohydr. Chem. 2:228 (1963); Bonner, W. A., J. Org. Chem., 26, 908–911 (1961)). The 5' esters of arabinofuranosyl compounds can be prepared according to Gish, D. T. et al J. Med. Chem. 14:1160 (1971) and Neil, G. L. et al, Can. Res. 30:1047–1054 (1970).

Preparation of the 2',3'-dideoxy compounds (single bond at position 2',3', See IIIa) is carried out by reduction of the double bond acylated analogues (or -4',6'-di-O-acyl analogue) with $B_2H_6$/THF. The reduced compounds can then be hydrolyzed with ammonia, supra.

The TMS protected 2-nitroimidazole can be prepared from 2-nitroimidazole with hexamethyldisilazane or bis(trimethylsilyl)acetamide(BSA) or trimethylsilyl chloride, according to well known procedures (Prisbe, E. J. et al, J. Org. Chem. 43: 4784–4794 (1978)).

The preparation of nonhydroxylated pyranosyl or furanosyl compounds of the invention can be prepared by reaction of 2-nitroimidazole (or derivatives) with dihydrofuran or dihydropyran, according to the following scheme:

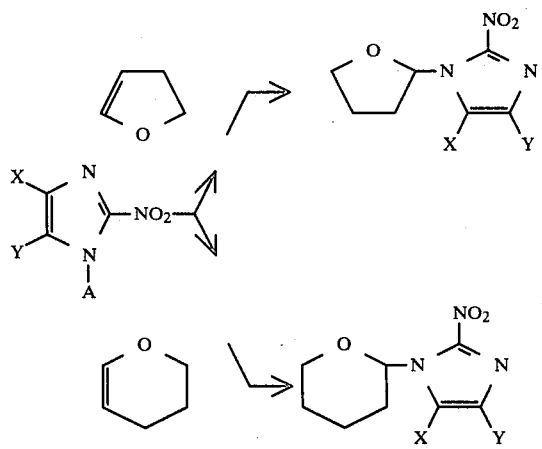

These condensations are preferably carried out in the presence of acid, such as p-toluenesulfonic acid.

The preparation of carbocyclic analogues of the pyranosyl or furanosyl compounds of the invention can be carried out by condensing cyclopentene oxide or cyclohexene oxide with 2-nitroimidazole in the presence of base, according to the following scheme:

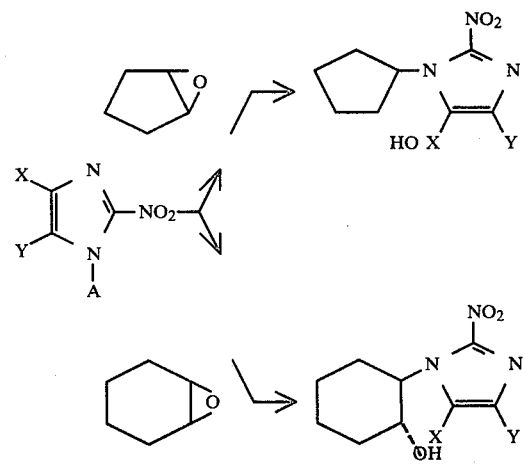

The acyclic ether nucleoside analogue may be prepared by nucleophilic condensation of TMS-protected 2-nitroimidazole with the appropriate ether containing a leaving group:

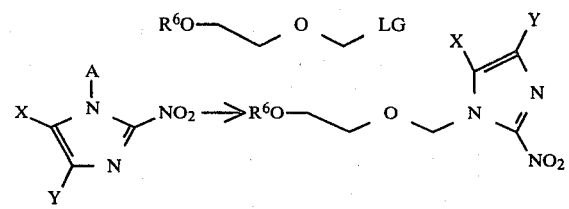

The preparation of substituted and unsubstituted 2-nitroimidazoles may be carried out as follows:

1. 4 (or 5)-acyl substituted 2-nitroimidazole. These may be prepared by oxidation of the corresponding 4 (or 5)-acyl substituted 2-aminoimidazoles with, for example, $NaNO_2$-Cu under acidic conditions or other such mild oxidizing agents. The 2-amino 4(5)-acylimidazoles can be prepared following the methods of Braun et al in Journal of the American Chemical Society 100:4208 (1978).

2. 2-nitro-benzimidazoles. These may be prepared by the general methodology of Beaman et al (Antimicrobial Agents and Chemotherapy, 469 (1965)), herein incorporated by reference.

3. 2, 4(or 5)-dinitroimidazoles. 2-nitroimidazole prepared as described in (2) above, can be further nitrated in the presence of acetic anhydride, with fuming nitric acid to yield 2,4(or 5)-dinitroimidazole. These compounds are also described in Lancini, G. C., et al, Farmaco. Ed. Sci., 18:390 (1963).

4. Other substituted 2-nitroimidazoles. 2-nitroimidazoles substituted at position 4 or 5 with $C_1$-$C_4$ alkylcarboxy; nitrile; carboxyamide, $C_1$-$C_4$ nitrone, hydroxymethyl, nitrilomethyl, 2-phenylvinyl or 2-(nitrophenyl) vinyl, may all be prepared from the common intermediate 2-nitro-4(or 5)-formylimidazole:

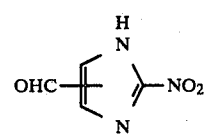

This formyl derivative, prepared by the methodology of Cavalleri et al (Journal of Heterocyclic Chemistry 9:979 (1972)), can be oxidized with chromium oxide and subsequently esterified to yield the alkyl carboxy derivative; it can be reduced with sodium borohydride to yield the hydroxymethyl derivative, which in turn can be chlorinated with $SOCl_2$ and further reacted with alkali metal cyanide (sodium cyanide for example) to yield the nitrilomethyl derivative. The 4(5) formyl derivative can also be treated with $C_1$-$C_4$ alkyl hydroxylamine (alkyl NH—OH) to yield the corresponding nitrones, according to Fieser and Fieser, Reagents for Organic Synthesis, Volume 6, page 538. The formyl derivative can also be reacted with $NH_2OSO_3H$ to give the nitrile derivative, which in turn can be hydrated to yield a carboxyamide derivative. The 2- phenyl vinyl derivative or its nitrated analog may be obtained as an intermediate of the aforementioned Cavalleri et al synthesis. All of the aforementioned single reactions are very well known to those in the art and details for their conditions and features can be readily ascertained without undue experimentation, by reference to standard synthetic textbooks in organic chemistry.

The compounds of this invention can be administered by any means that effect the radiosensitization of hypoxic tumor cells in patients undergoing X-ray radiotherapy. For example, administration can be parenterally, subcutaneously, intravenously, intramuscularly or intraperitoneally. Alternatively or concurrently, administration can be by the oral route. The dosage administered will be dependent upon the age, health and weight of the recipient, kind of concurrent treatment if any, frequency of treatment, and the nature of the effect desired. Generally, a dosage of active ingredient compounds will be from about 0.5 mg to 100 mg per kg of body weight. Normally, from 1 to 50 mg per kg per application, in one or more applications per radiotherapy, is effective to obtain the desired result.

It is known that in the X-ray radiotherapy of cancers, the particular radiation dose to be utilized depends on a large variety of factors, which factors are independent of the presence or absence of radiosensitizers. Thus, the dosages of X-rays used in the present invention are fixed by the particular requirements of each situation. The dosage will depend on the size of the tumor, the location of the tumor, the age and sex of the patient, the frequency of the dosage, the presence of other tumors, possible metastases, and the like. The presence of the radiosensitizers increases the kill ratio of tumor to non-tumor cells. The pre-set dosage radiation therefore becomes more effective in the presence of the radiosensitizers of the invention that in their absence. Those skilled in the art of radiotherapy can readily ascertain the dosage for any particular tumor, by reference to the following two textbooks: Andrews, R. "The Radiobiology of Human Cancer Radiotherapy", Second Edition, University Park Press, 1978, especially chapter 25 thereof; Gilbert, H. A., and Kagan, A. R., Ed. Harper and Row, 1978 "Modern Radiation Oncology, Classic Literature and Current Management". These books are herein incorporated by reference.

The compounds can be employed in dosage forms such as tablets, capsules, powder packets or liquid solutions, suspensions or elixirs for oral administration, or sterile liquids for formulations such as solutions or suspensions for parenteral use. In such compositions, the active ingredient will ordinarily always be present in an amount at least 0.5% by weight based upon the total weight of the composition and not more than 90% by weight. An inert, pharmaceutically acceptable carrier is preferably used.

Having now generally described this invention, a more complete understanding can be obtained by reference to certain Examples, which are included for purposes of illustration only and are not intended to be limiting unless otherwise specified.

CHEMICAL PREPARATIONS

EXAMPLE 1.1

Synthesis of
1-(2',3',5'-tri-O-benzoyl-α-D-arabinofuranosyl)-2-nitroimidazole and
1-(2',3',5'-tri-O-benzoyl-β-D-arabinofuranosyl)-2-nitroimidazole To a crude solution of trimethylsilyl-2-nitroimidazole (from 1.72 g (0.015 mol)) of 2-nitroimidazole according to Prisbe et al (Journal of Organic Chemistry 43:4784 (1978)) in anhydrous acetonitrile (100 ml) was added 5.25 g (0.01 mol) of 1-bromo-2,3,5-tri-O-benzoyl-D-arabinofuranose (Fletcher, J. R. Methods Carbohydrate Chemistry 2: 228 (1963)) in anhydrous acetonitrile (50 ml) and 3.60 g (0.01 mol) of mercuric bromide. The resulting solution was stirred for two days at room temperature and then evaporated to dryness. A filtered solution of the residue in chloroform (300 ml) was washed with 30% potassium iodide, saturated aqueous sodium bicarbonate, and water. The organic phase was dried and evaporated to dryness. The residual syrup was chromatographed on a column of silica gel G using benzene-ethylacetate (10:1 to 0:1) to give 0.4 g (7.2%) of the β derivative (mp 124° C. from the initial fractions), and 1.83 g (32.9%) of the α derivative (mp 82° C. from the latter fractions).

EXAMPLE 1.2

Synthesis of 1-α-D-Arabinofuranosyl-2-nitroimidazole 1-(2',3',5'-tri-O-benzoyl-α-D-arabinofuranosyl)-2-nitroimidazole (557 mg, 1 mmol) was added to 5 ml of 0.05 M methanolic sodium methoxide. The mixture was stirred at 0° C. for 2.5 hours. The precipitate of 1-(mono-benzoyl-α-D-arabino furanosyl)-2-nitroimidazole was filtered off and the filtered solution was purified by preparative TLC using chloroform:methanol (5:1) to give 115 mg (46.9%) of the title product as pale yellow needles, mp 160° C.

EXAMPLE 1.3

Synthesis of 1-(β-D-Arabinofuranosyl)-2-nitroimidazole 1-(2',3',5'-tri-O-benzoyl-β-D-arabinofuranosyl)-2-nitroimidazole (150 mg, 0.27 mmol) was added to 2.5 ml of 0.025 M methanolic sodium methoxide. The mixture was stirred at 0° C. for three hours and then purified by preparative TLC using chloroform:methanol (6:1) to give 36 mg (54.6%) of the title product as white needles, mp 172° C.

EXAMPLE 1.4

Synthesis of
1-(4',6'-di-O-acetyl-2',3'-didehydro-2',3'-dideoxy-α-D-erythro-hexopyranosyl)-2-nitroimidazole and
1-(4',6'-di-O-acetyl-2',3-didehydro-2',3'-dideoxy-β-D-erythro-hexopyranosyl)-2-nitroimidazole (a) Stannic Chloride (3.5 ml, 30 mmol) was added to a solution of TMS-2-nitroimidazole derivative (from 2.0 g, (17.7 mmol) of 2-nitroimidazole) and 3.32 g (10 mmol) of 1,3,4,6-tetra-O-acetyl 2-deoxy-D-glucose in 1,2-dichloroethane (100 ml). The mixture was heated at 60°–70° C. for 45 minutes and then washed with saturated aqueous sodium bicarbonate and water. The organic phase was dried and evaporated to dryness. Preparative TLC using benzene-ethyl acetate (3:2) gave two major bands. Elution of the faster one produced 0.17 g (5.2%) of product as white needles (mp 136° C.). Elution of the slower band yielded 0.49 g (15.1%) of the product as white needles (mp 124° C.).

(b) 2-nitroimidazole (2.48 g, 0.02 mmol) and 3,4,6-tri-O-acetylglucal (5.80 g, 0.02 mmol) were thoroughly mixed and heated at 120° C. (oil bath) in vacuo for 5 minutes. Then, p-toluene-sulfonic acid (30 mg) was added and the mixture was heated at 120° C. to 140° C. (oil bath) in vacuo for additional 20 minutes. A filtered solution of the residue in chloroform (200 ml) was washed with saturated aqueous sodium bicarbonate and water. The organic phase was dried and evaporated to dryness. The residual syrup was chromatographed on a column of silica gel G using benzene-ethylacetate (4:1 to 1:1) to give 0.45 g (6.9%) of the α product from the initial factions, 0.54 g (8.3%) of the β product from the latter factions, and an additional compound which was isolated from the last fractions as minor products, the structures of which was confirmed by NMR as follows:

EXAMPLE 1.5

Synthesis of 1-(2',3'-didehydro-2',3'-dideoxy-α-D-erythro-hexopyranosyl)-2-nitroimidazole A solution of the diacetyl starting material prepared in Example 1.4 (325 mg, 1 mmol) in 15 ml of presaturated methanolic ammonia was stored at 0° C. for overnight and then evaporated. The solid residue was crystallized from ethanol to leave 160 mg (66.3%) of the title product as colorless prisms, mp 152° C.

EXAMPLE 1.6

Synthesis of 1-(2',3'-didehydro-2',3'-dideoxy-β-D-erythro-hexopyranonyl)-2-nitroimidazole A solution of the diacetylated starting material from Experiment 1.4 (325 mg, 1 mmol) in 15 ml of presaturated methanolic ammonia was stored at 0° C. for overnight and then evaporated. The residue was purified by preparative TLC using chloroform:methanol (5:1) to give 230 mg (95.4%) of the title product as an amorphous compound.

EXAMPLE 1.7

2-Amino-1-(4',6'-di-O-acetyl-2',3'-dideoxy-β-D-erythro-hexopyranosyl)-imidazole

A solution of 0.5 g (1.54 mmol) of the 2',3'-didehydro analog in 50 ml of ethanol was hydrogenated at room temperature for 1 hr. in the presence of 0.5 g of 5% Pd/C. The catalyst was removed by filtration and washed with 30 ml of ethanol. The solution was evaporated under vacuum to give 0.45 g (98%) of the amino derivative which was employed directly for further reaction.

EXAMPLE 1.8

1-(4',6'-Di-O-acetyl-2',3'-dideoxy-β-D-erythro-hexopyranosyl)-2-nitroimidazole

To a stirred solution of 0.45 g (1.5 mmol) of the amino analog in 3.5 ml of water and 3.5 ml of 50% fluoboric acid cooled at −15° C. was added dropwise a solution of 1.4 g of sodium nitrite in 3 ml of water. The mixture was stirred for 30 min at −15° C. and then a suspension of 1.5 g of copper powder in a solution of 5.0 g of sodium nitrite in 10 ml of water was added slowly at 0° C. The mixture was stirred at 0° C. for 1 hr. and then at room temperature for 16 hr. The suspension was extracted with ethyl acetate, the extracts washed with saturated sodium bicarbonate and water, dried and evaporated. The residue was purified by preparative TLC to yield 0.025 g (5.1%) of the title compound as colorless needles, mp 137°-138° C.

The α-isomer has also been synthesized by utilizing a similar procedure.

EXAMPLE 1.9

Synthesis of 1-(3,5-di-O-acetyl-2-deoxy-α, β-D-erythro-pentofuranosyl)-2-nitroimidazole A mixture of 1.7 g (15 mmol) of 2-nitroimidazole and 5.2 g (20 mmol) of 1,3,5-tri-O-acetyl-2-deoxyribose [synthesized by the procedure of Robins, M. J. and Robins, R. K., J. Am. Chem. Soc. 87, 4934 (1965)] was fused at 130° C. in the presence of 50 mg of zinc chloride under reduced pressure (20 to 30 mm Hg) for 40 min, according to the procedure of Whittle and Robins [J. Am. Chem. Soc. 87, 4940 (1965)]. The reaction mixture was dissolved in 200 ml of chloroform and filtered. The filtrate was washed with saturated aqueous sodium bicarbonate and water, dried and evaporated. The preparative TLC of the residual syrup with ethyl acetate-benzene (5:2) as eluant produced 0.32 g (6.8%) of α-isomer, mp 155° C. and 0.32 g (6.8%) as a syrup of β-isomer of the title compound.

EXAMPLE 1.10

1-(2-deoxy-α or β-D-erythro-pentofuranosyl)-2-nitroimidazole

A solution of 0.2 g (0.64 mmol) of either α or β isomer was dissolved in 15 ml of methanol saturated with ammonia at 0°-5° C. and stirred for 15 hr. The solution was then evaporated and the residue was crystallized from ethanol-petroleum ether to yield 0.063 g (43.2%) of α-isomer, mp 110° C. and 0.053 g (36%) of β-isomer, mp 225° C. dec.

EXAMPLE 1.11

1-(Tetrahydro-2-furanyl)-2-nitroimidazole

A suspension of 0.338 g (3.0 mmol) of 2-nitroimidazole and 0.7 ml of 2,3-dihydrofuran in 35 ml of acetonitrile was stirred at 35°-45° C. in the presence of 5 mg of p-toluenesulfonic acid for 2 hr. under nitrogen and then evaporated. The residue was dissolved in chloroform, filtered, and evaporated to yield a syrup which was purified by preparative TLC with ethyl acetate-benzene (1:1) to provide 0.41 g (75.3%) of the title compound, mp 91° C.

EXAMPLE 1.12

1-(Tetrahydro-2-pyranyl)-2-nitroimidazole

A suspension of 0.113 g (1.0 mmol) of 2-nitroimidazole and 10 ml of 2,3-dihydropyran was stirred at 80° C. in the presence of 5 mg of p-toluenesulfonic acid for 1 hr. according to the procedure of Robins et al. [J. Am. Chem. Soc 83, 2574 (1961)]. The excess of 2,3-dihydropyran was removed under reduced pressure. The residue was chromatographed on silica gel by elution with ethyl acetate-benzene mixture (employing a gradient from 9:1 to 1:1) to provide 0.165 g (83.7%) of the title compound, which was recrystallized from petroleum ether, mp 50° C.

EXAMPLE 1.13

1-(2-Hydroxycyclopentyl)-2-nitroimidazole

A suspension of 0.339 g (3 mmol) of 2-nitroimidazole, 30 ml of ethanol, 3.5 ml of cyclopentene oxide and 0.15 g of potassium carbonate was refluxed with stirring under nitrogen for 20 hr. A clear yellow solution resulted; this was evaporated and the residue dissolved in 50 ml of chloroform and filtered. The filtrate was evaporated to yield 0.28 g (47.3%) of the title compound. It was recrystallized from ethyl acetate, mp 109° C.

EXAMPLE 1.14

1-(2-Hydroxycyclohexyl)-2-nitroimidazole

A suspension of 0.565 g (5 mmole) of 2-nitroimidazole, 50 ml of ethanol, 5.0 ml of cyclohexene oxide, and 0.25 g of potassium carbonate was refluxed with stirring under nitrogen for 16 hr. The resulting yellow solution was evaporated and the residue dissolved in 100 ml of chloroform and filtered. The filtrate was evaporated and the residue purified by preparative TLC with ethyl acetate: benzene (2:1) as eluant to provide 0.359 g (34.0%). It was recrystallized from ethyl acetate-ether, mp 141° C.

EXAMPLE 1.15

1-{[2-Benzoyloxy)ethoxy]methyl}-2-nitroimidazole

A solution of 1.13 g (0.01 mol) of trimethylsilyl derivative of 2-nitroimidazole [synthesized according to Prisbe et al., J. Org. Chem. 43, 4784 (1978)], 6.44 g (0.03 mol) of 2-(benzoyloxy)ethoxymethyl chloride [synthesized according to Schaeffer et al., Nature 272, 583 (1978)] and 7.2 g (0.02 mol) of mercuric bromide in 100 ml of acetonitrile was stirred at ambient temperature for 16 hr. The reaction mixture was then evaporated and the residue extracted with chloroform. The extracts were filtered, washed successively with saturated aqueous sodium bicarbonate solution, 30% potassium iodide solution, and water. The chloroform layer was dried and evaporated under vacuum. The residual syrup was purified by preparative TLC with benzene:ethyl acetate (5:3) to yield 0.71 g (24.4%) of the title compound as amorphous material.

EXAMPLE 1.16

1-[(2-hydroxyethoxy)methyl]-2-nitroimidazole

A solution of 0.5 g (1.72 mmol) of the benzoyloxy derivative in 70 ml of methanol saturated with ammonia was slowly stirred at 0°–5° C. for 16 hr. and then evaporated under vacuum at ambient temperature. The residual gummy solid was purified by preparative TLC with ethyl acetate and recrystallized from ethanol to yield 0.144 g (48.0%) of the title compound, mp 115° C.

EXAMPLE 2

Biological Experimentation 2.1 In vitro Cytotoxicity Experiments

Asynchronous monolayers of cultures of Chinese hamster cells line V-79 were employed in all experiments. The monolayers were derived from exponentially growing cultures. Methods of culturing and handling have been reported earlier by Cooke et al, Rad. Res. 65, 152 (1976). The plated cultures were rendered hypoxic in sealed dural containers capable of holding seven petri dishes, by purging with nitrogen (oxygen-free grade) for one hour. Irradiation was carried out by using a cobalt-60 source at a dose rate of approximately 240 rad/min according to the procedure described by Agrawal et al Rad. Res. 78:532 (1979). A dose of 1400 rad was given to hypoxic cells in glass petri dishes in the presence of a given drug concentration (2000 cells/dish). Cell survival was estimated from unirradiated toxic hypoxic cells exposed to the same drug concentration. Complete survival curves were obtained for each compound at the radiation doses of 400 to 3000 rad. The $D_o$ value was calculated for each compound and the ratio of the $D_o$ value for the hypoxic control cells to the $D_o$ value of the hypoxic drug treated cells provided the sensitized enhancement ratio of the corresponding agent.

Cultures were incubated for 6 days at 37° C. in an atmosphere of 5% $CO_2$. The resulting colonies were fixed in absolute ethanol and stained with methylene blue and counted.

To determine toxicity in vitro, glass petri dishes containing approximately 200 Chinese hamster cells/dish were exposed to a range of concentrations of each drug for 2 hours and/or 4 hours at 37° C. Drug concentrations between 10 μM and 0.5 mM were employed initially. The biological results are shown in Table 1.

| | Compounds(See legend) | | | | | |
|---|---|---|---|---|---|---|
| | A | B | C | D | E | F |
| Radiosensitization (enhancement ratio in Chinese hamster cells) | 2.0 at 0.25 mM<br>2.2 at 0.5 mM | 2.0 at 0.5 mM | 1.6 at 0.5 mM | 1.7 at 1.0 mM | 1.0 at 0.05 mM | 1.1 at 0.1 mM |
| In vitro cytotoxicity in oxic cells (% survival at 2 hours) | 82.4% at 1.0 mM<br>90.0% at 0.5 mM<br>104.0% at 0.25 mM<br>99.0% at 0.1 mM | 106 at 0.01 mM<br>100 at 0.05 mM<br>103 at 0.1 mM<br>100 at 0.5 mM | 101 at 0.01 mM<br>100 at 0.05 mM<br>95 at 0.1 mM<br>97 at 0.5 mM | 105 at 0.1 mM<br>104 at 0.5 mM<br>99 at 1.0 mM<br>116 at 5.0 mM | | |
| In vitro cytotoxicity in oxic cells (% survival at 4 hours) | 104% at 0.25 mM<br>99.0% at 0.1 mM | 100 at 0.01 mM<br>100 at 0.05 mM<br>101 at 0.1 mM<br>102 at 0.5 mM | 101 at 0.1 mM<br>103 at 0.5 mM<br>94 at 0.1 mM<br>88 at 0.5 mM | | | |
| In vitro cytotoxicity in hypoxic cells (% survival at 2 hours) | 59.6% at 1.0 mM<br>75.9% at 0.5 mM<br>92.0% at 0.25 mM<br>97.3 at 0.1 mM | 100.4% at 0.5 mM<br>90.9% at 0.1 mM | 92.6% at 0.5 mM<br>103.5% at 0.1 mM | | 104 at 0.1 mM<br>84 at 0.05 mM<br>66 at 0.1 mM<br>12 at 0.25 mM | 102 at 0.01 mM<br>102 at 0.05 mM<br>97 at 0.1 mM<br>105 at 0.25 mM |
| In vitro cytotoxicity in hypoxic cells (% survival at 4 hours) | 0.0% at 1.0 mM<br>15.8% at 0.5 mM<br>26.7% at 0.25 mM<br>56.7% at 0.1 mM | 60.3% at 0.5 mM<br>96.0% at 0.1 mM | 41.1% at 0.5 mM<br>86.6% at 0.1 mM | | 80 at 0.01 mM<br>76 at 0.05 mM<br>46 at 0.1 mM<br>2.6 at 0.25 mM | 103 at 0.01 mM<br>104 at 0.05 mM<br>89 at 0.1 mM<br>73 at 0.25 mM |
| Differential toxicity to hypoxic cells at 4 hours | Yes | Yes | Yes | | | |
| $LD_{50}$ in mice | 3.3 g/kg | | | | | |
| | G | H | I | J | K | L |
| Radiosenitization | 1.9 at 1.0 mM | 1.9 at 1.0 mM | 1.6 at 1.0 mM | 1.7 at 1.0 mM | 2.0 at 1.0 mM | 2.0 at 1.0 mM |

| | Compounds(See legend) | | | | | |
|---|---|---|---|---|---|---|
| (enhancement ratio Chinese hamster cells) | | | | | | |
| In vitro cytoxicity in oxic cells (% survival at 2 hours) | 82.4% at 5.0 mM 93.0% at 1.0 mM 88.9% at 0.5 mM 95.3% at 0.1 mM | 81.3% at 5.0 mM 98.2% at 1.0 mM 94.2% at 0.5 mM 95.3% at 0.1 mM | 79.5% at 5.0 mM 87.1% at 1.0 mM 100.6% at 0.5 mM 98.8% at 0.1 mM | 94.9% at 5.0 mM 105.1% at 1.0 mM 100.6% at 0.5 mM 105.6% at 0.1 mM | 94.7% at 5.0 mM 106.8% at 1.0 mM 110.2% at 0.5 mM 111.6% at 0.1 mn | 86.0% at 1.0 mM 90.3% at 0.5 mM 98.2% at 0.1 mM |
| In vitro cytoxicity in oxic cells (% survival at 4 hours) | | | | | | |
| In vitro cytoxicity in hypoxic cells (% survival at 2 hours) | | | | | | |
| In vitro cytoxicity in hypoxic cells (% survival at 4 hours) | | | | | | |
| Differential toxicity to hypoxic cells at 4 hours | | | | | | |
| LD$_{50}$ in mice | | | | | | |

| | M | N | O |
|---|---|---|---|
| Radiosensitization (enhancement ratio Chinese hamster cells) | 2.1 at 1.0 mM | 2.1 at 1.0 mM | 1.5 at 1.0 mM |
| In vitro cytoxicity in oxic cells (% survival at 2 hours) | 103.9% at 1.0 mM 105.8% at 0.5 mM 99.5% at 0.1 mM | | |
| In vitro cytoxicity in oxic cells (% survival at 4 hours) | | | |
| In vitro cytoxicity in hypoxic cells (% survival at 2 hours) | | | |
| In vitro cytoxicity in hypoxic cells (% survival at 4 hours) | | | |
| Differential toxicity to hypoxic cells at 4 hours | | Yes | Yes |
| LD$_{50}$ in mice | | 1.4–1.6 g/kg | 3/5 g/kg |

Compounds:
A 1-(2',3'-didehydro-2',3'-dideoxy-α-D-erythro-hexopyranonyl)-2-nitroimidazole.
B 1-(4',6'-di-O—acetyl-2',3'-didehydro-2',3'-dideoxy-α-D-erythro-hexopyranosyl)-2-nitroimidazole.
C 1-(4',6'-di-O—acetyl-2',3'-didehydro-2',3'-dideoxy-β-D-erythro-hexopyranosyl)-2-nitroimidazole.
D 1-(α-D-Arabinofuranosyl)-2-nitroimidazole.
E 1-(2',3',5'-tri-O—benzoyl-α-D-arabinofuranosyl)-2-nitroimidazole.
F 1-(2',3',5'-tri-O—benzoyl β-D-arabinofuranosyl)-2-nitroimidazole.
G 1-(2-deoxy-α-D-erythro-pentofuranosyl)-2-nitroimidazole.
H 1-(2-deoxy-β-D-erythro-pentofuranosyl)-2-nitroimidazole.
I 1-(Tetrahydro-2-furanyl)-2-nitroimidazole.
J 1-(Tetrahydro-2-pyranyl)-2-nitroimidazole.
K 1-(2-Hydroxycyclopentyl)-2-nitroimidazole.
L 1-(2-Hydroxycyclohexyl)-2-nitroimidazole.
M 1-[(2-hydroxyethoxy)methyl]-2-nitroimidazole.
N Misonidazole.
O Metronidazole.

As this data indicates, the compounds of the present invention have toxicity and radiosensitization characteristics which make them ideal for use in radiotherapy treatment of humans. The fully acylated derivatives are radiosensitizers but, because of their poor solubility, are somewhat less desirable.

2.2 In vivo neurotoxicity

Neurotoxicity in mice was determined using mice of strain CDF$_1$. This was carried out by (1) determining the LD$_{50}$ of each compound in mice and (2) observing the animals for acute neurotoxic symptoms such as convulsions. The drugs were either solubilized or suspended in normal saline and administered intraperitoneally to groups of ten mice. The mice were observed for 24 hours for acute toxicity and death. Results are indicated at Table 1.

2.3 Pharmacokinetics of 1-(2',3'-didehydro-2',3'-dideoxy-α-D-erythro-hexopyranosyl)-2-nitroimidazole The drug solution was made in normal saline at a concentration of 50 mg/ml. The drug solution was injected intraperitoneally at a dose level of 1 g/kg to C57/BL mice bearing 15 day old B16 melanoma tumor. At 30 and 60 minute interval after the drug administration, mice were anesthetized, blood sample was taken directly by heart puncture and tumor and brain tissue were removed. Plasma was separated after centrifugation of the whole blood and extracted with methanol. Brain and tumor tissue were homogenized and also extracted with methanol. The methanol extracts were analyzed by reverse phase high-performance liquid chromatography employing 25% methanol as mobile phase. The peak was detected at 320 nm with a retention time of 2.3 min. The flow rate was 2 ml/min. Table 2 shows localization in tissue data for the title compound.

TABLE 2

| Time | Plasma μg/ml | Brain μg/g | (B$_{16}$ melanoma) μg/g |
|---|---|---|---|
| 30 min | 1053 | 102 | 293 |
| 60 min | 648 | 120 | 346 |
| | Ratio of Tumor/plasma | Ratio of Brain/Plasma | Ratio of Tumor/Brain |
| 30 min | 0.278 | 0.097 | 2.87 |
| 60 min | 0.534 | 0.18 | 2.88 |

The data for misonidazole is as follows: the ratio tumor/plasma is 0.54; the ratio brain/plasma is 0.51 or higher (British Journal of Cancer, 40:335 (1979)).

The results demonstrate that Ratio of Tumor/Plasma has increased with time indicating concentration of drug in the tumor. Although the ratio of Brain/Plasma has also increased with time, tumor concentration remains approximately 3-fold higher as shown by the Tumor/Brain ratio.

Having now fully described this invention, it will be apparent to one skilled in the art that many modifications and variations can be carried out without changing the scope or spirit thereof.

What is claimed as new and desired to be secured by Letters Patent of the United States is:

1. A compound of the formula:

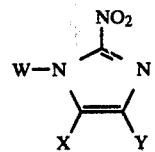

wherein W is selected from the group consisting of:

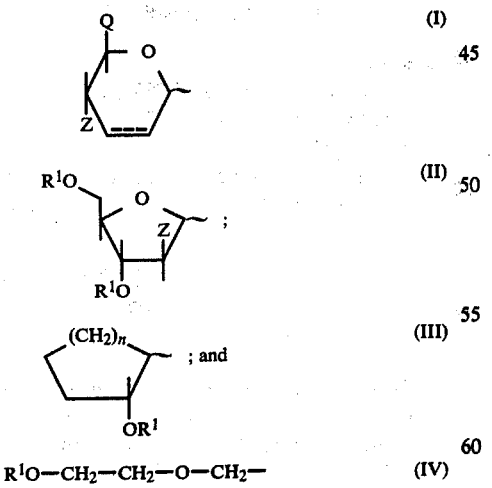

wherein
Q is hydrogen or —CH$_2$OR$^1$;
Z is hydrogen or —OR$^1$;
n is 1 or 2:
R$^1$ are the same or different radicals selected from the group consisting of hydrogen, and

where
R$^2$ is lower alkyl, phenyl or lower alkylaryl;
wherein the bond between carbons 2' and 3' in structure I may be single or double; and wherein X and Y are the same or different selected from the group consisting of hydrogen,

where R$^3$ is C$_1$-C$_4$ alkyl, nitrile; carboxyamide;

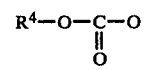

where R$^4$ is C$_1$-C$_4$ alkyl; R$^5$—N(O)=CH— where R$^5$ is C$_1$-C$_4$ alkyl; HOCH$_2$—; NC—CH$_2$—; 2-phenylvinyl and 2-(nitrophenyl)vinyl and esters of said compounds.

2. The compound claim 1 wherein R$^1$ is hydrogen.
3. The compound of claim 1 wherein R$^1$ is

4. The compound claim 3 wherein the configuration around the C-1' of the ring is α.
5. The compound of claim 1 wherein the configuration around the C-1' carbon of the ring is β.
6. The compound claim 1 wherein X=Y=hydrogen.
7. The compound of claim 1 which is

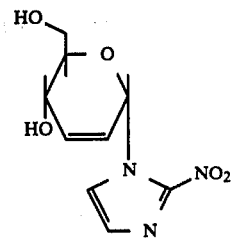

8. The compound of claim 1 which is

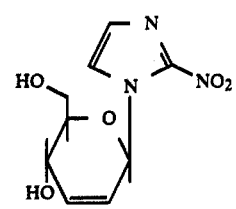

9. The compound of claim 1 which is

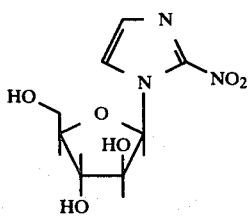

10. The compound of claim 1 which is

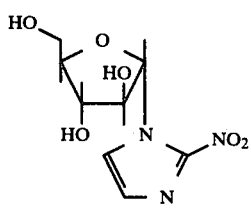

11. The compound of claim 1 which is

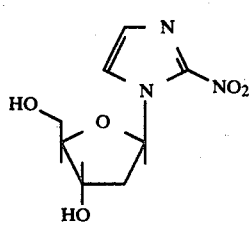

12. The compound of claim 1 which is

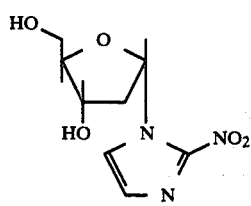

13. The compound of claim 1 which is

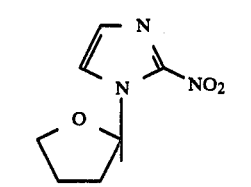

14. The compound of claim 1 which is

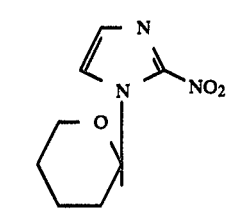

15. The compound of claim 1 which is

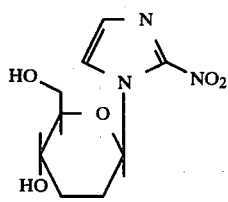

16. A pharmaceutical composition useful for the radiosensitation of hypoxic tumor cells which comprises a radiosensitizing amount of a compound of the formula:

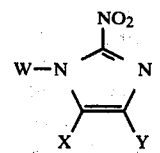

wherein W is selected from the group consisting of:

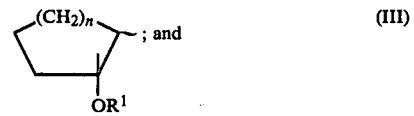

wherein
Q is hydrogen or —CH$_2$OR$^1$;
Z is hydrogen or —OR$^1$;
n is 1 or 2:
R$^1$ are the same or different radicals selected from the group consisting of hydrogen, and

where
R$^2$ is lower alkyl, phenyl, or lower alkylaryl;
wherein the bond between carbons 2' and 3' in structure I may be single or double; and wherein X and Y are the same or different selected from the group consisting of hydrogen,

where R$^3$ is C$_1$-C$_4$ alkyl; nitrile; carboxyamide;

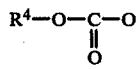

where R[4] is $C_1$-$C_4$ alkyl; R[5]—N(O)=CH— where R[5] is $C_1$-$C_4$ alkyl; HOCH$_2$—; NC—CH$_2$; 2-phenyl-vinyl and 2-(nitrophenyl)-vinyl and esters of said compounds.

17. The composition of claim 16 wherein R[1] is hydrogen.

18. The composition of claim 16 wherein R[1] is

19. The composition of claim 16 wherein the configuration around the C-1' carbon of the nucleoside ring is α.

20. The composition of claim 16 wherein the configuration around the C-1' carbon of the nucleoside ring is β.

21. The composition of claim 16 wherein X=Y=hydrogen.

22. The composition of claim 16 wherein said compound is

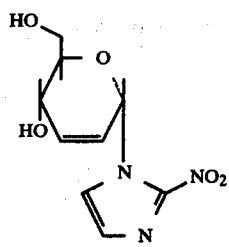

23. The composition of claim 16 wherein said compound is

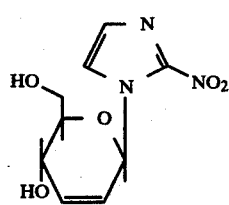

24. The composition of claim 16 wherein said compound is

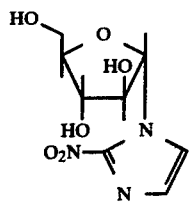

25. The composition of claim 16 wherein said compound is

26. The composition of claim 16 which is

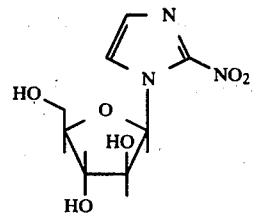

27. The composition of claim 16 which is

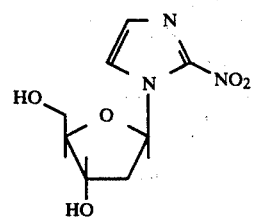

28. The composition of claim 16 which is

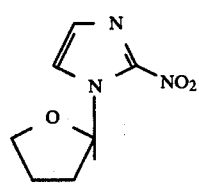

29. The composition of claim 16 which is

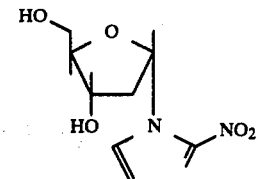

30. The composition of claim 16 which is

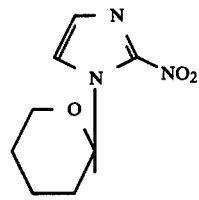

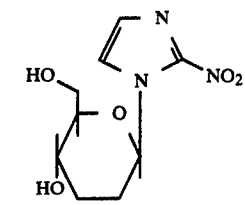

31. A method of radiosensitizing hypoxic tumor cells during X-ray radiotherapy in a mammal which comprises administering to said mammal a radiosensitizing amount of a compound of claim 1.
32. The compound of claim 1 which is
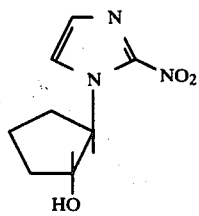
33. The compound of claim 1 which is
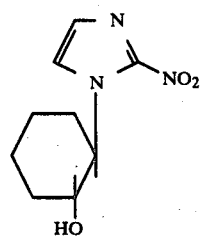
34. The compound of claim 1 which is
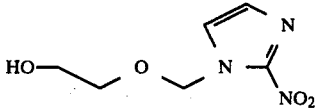
35. The composition of claim 16 which is
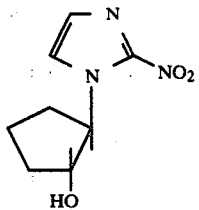
36. The composition of claim 16 which is
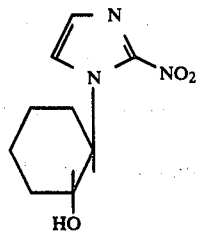
37. The composition of claim 16 which is
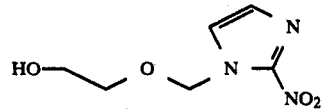
* * * * *